United States Patent [19]

Buethe et al.

[11] Patent Number: 4,611,083

[45] Date of Patent: Sep. 9, 1986

[54] LIQUID, UREA GROUP-CONTAINING POLYISOCYANATE MIXTURES

[75] Inventors: Ingolf Buethe, Boehl-Iggelheim; Matthias Marx, Bad Durkheim; Willibald Schönleben, Heidelberg, all of Fed. Rep. of Germany

[73] Assignee: BASF Aktiengesellschaft, Ludwigshafen, Fed. Rep. of Germany

[21] Appl. No.: 674,077

[22] Filed: Nov. 23, 1984

[30] Foreign Application Priority Data

Nov. 26, 1983 [DE] Fed. Rep. of Germany ....... 3342564

[51] Int. Cl.[4] ......................................... C07C 119/048
[52] U.S. Cl. .................................. 560/351; 560/359; 521/159
[58] Field of Search ................ 260/453 AM, 453 AB; 560/359, 351

[56] References Cited

U.S. PATENT DOCUMENTS 3,441,588  4/1969  Wagner et al. .............. 260/453 AB

*Primary Examiner*—Dolph H. Torrence
*Attorney, Agent, or Firm*—D. Barbara McKenzie; Joseph D. Michaels

[57] ABSTRACT

The invention relates to urea group-containing polyisocyanate mixtures which are liquid at room temperature and have an isocyanate group content of from 15 to 30 weight percent and a diphenylmethane diisocyanate content of from 55 to 90 weight percent, obtained through the reaction of (A) polyoxyalkylene polyamines having a functionality of from 2 to 5 and an amine number from 20 to 250 with a polyisocyanate (B) selected from the group consisting of (B1) a mixture of diphenylmethane diisocyanates and polyphenyl polymethylene polyisocyanates having a diphenylmethane diisocyanate content of from 55 to 90 weight percent or (B2) at least one diphenylmethane diisocyanate isomer.

The polyisocyanate mixtures claimed in the invention are used to prepare dense or cellular polyurethane and-/or polyisocyanurate plastics, in particular, flexible polyurethane foams.

2 Claims, No Drawings

LIQUID, UREA GROUP-CONTAINING POLYISOCYANATE MIXTURES

BACKGROUND OF THE INVENTION

1. Field of the Invention

This invention relates to modified polyisocyanates and to the plastics derived therefrom. More specifically, it relates to urea group-containing polyisocyanates and flexible polyurethane foams based on these products.

2. Description of the Prior Art

Urethane, allophanate biuret, urea, carbodiimide, and/or isocyanurate group-containing organic polyisocyanates, which are generally dissolved in unmodified polyisocyanates, of the same type, are the subject of numerous patents and patent applications. For example, urethane group-containing polyisocyanates are found in DE application No. 25 13 793 (GB Pat. No. 1,450,660) and DE application No 25 13 796 (GB Pat. No. 1,444,192); allophanate group-containing polyisocyanates, in GB Pat. No. 994,890; biuret group-containing polyisocyanates, in DE application No. 1,215,365 (U.S. Pat. No. 3,441,588); urea group-containing polyisocyanates, in DE application No. 1,008,484 (GB Pat. No. 791,852); carbodiimide group-containing polyisocyanates, in EP application No. 57,862; and isocyanurate group-containing polyisocyanates, in DE Pat. No. 2,616,416 (GB Pat. No. 1,571,933).

In this way, polyisocyanates which are solid at room temperature can be liquified to improve processibility or, for liquid polyisocyanates having a high vapor pressure, volatility can be reduced by increasing the molecular weight.

As specified in European Pat. Nos. 4617, 4618, and 4879, flexible polyurethane foams having high load-bearing and impact absorption ability, or low flammability, can be prepared from diphenylmethane diisocyanates and polyphenylpolymethylene polyisocyanates mixtures (subsequently referred to as crude MDI) having high contents of diphenylmethane diisocyanate (subsequently referred to as MDI), or urethane group-containing crude MDI. The disadvantage with this process is that the resistance of such flexible polyurethane foams to aging at elevated temperatures and high humidity, for example that required for upholstery cushioning material in the construction of automobiles, frequently is not adequately met.

SUMMARY OF THE INVENTION

The overall objective of this invention is the preparation of flexible polyurethane foams having good resistance to aging at high temperatures and humidities. This objective was unexpectedly met by using urea group-containing polyisocyanate mixtures modified with selected polyamines as the isocyanate component for the polyurethane formation.

Thus, the object of the invention is also a urea group-containing polyisocyanate mixture which is liquid at room temperature and which has an isocyanate group content of from 15 to 30 weight percent, preferably from 20 to 28 weight percent, and a diphenylmethane diisocyanate content of from 55 to 90 weight percent, preferably from 60 to 85 weight percent, whereby the weight percent is based on the total weight of the polyisocyanate mixture, and which is obtained by reacting (A) polyoxyalkylene polyamine having an amine functionality of from 2 to 5 and an amine number from 20 to 250 with an excess of a polyisocyanate (B) selected from the group consisting of (B1) a mixture of diphenylmethane diisocyanates and polyphenylpolymethylene polyisocyanates having a diphenylmethane diisocyanate content of from 55 to 90 weight percent, and (B2) at least one diphenylmethane diisocyanate isomer, and, where B2 is used, subsequently diluting the urea group-containing reaction product with a mixture of diphenylmethane diisocyanates and polyphenyl polymethylene polyisocyanates having a diphenylmethane diisocyanate content of from 30 to 85 weight percent.

The use of the products claimed in the invention to prepare dense or cellular polyurethane and/or polyisocyanurate plastics, in particular flexible polyurethane foams.

DESCRIPTION OF THE PREFERRED EMBODIMENTS

The following describes the initial components which can be used for the polyisocyanate mixtures claimed in the invention as well as the reactants used to prepare the polyurethane and/or polyisocyanurate plastics:

The polyoxyalkylene polyamine (A) is linear or branched, i.e., 2- to 5-functional, preferably a mixture with an average amine functionality of 2.1- to 3 and having an amine number from 20 to 250, preferably from 20 to 100.

Polyoxyalkylene polyamines of the following formulas have proven to be particularly successful and are, therefore, preferred:

$$H_2N-(R^2O)_x-R^1-NH_2,\quad H_2N-R^1-(OR^2)_x-NH-(R^2O)_y-R^1-NH_2$$

(I)  (II)

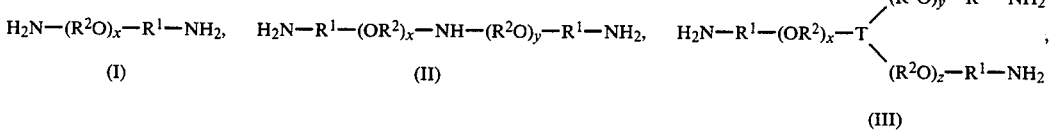

(III)

and

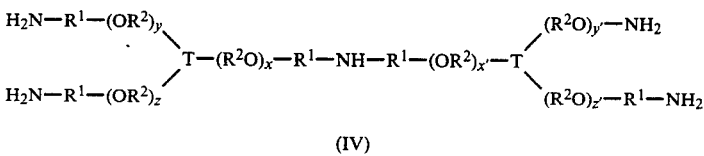

(IV)

where $R^1$ and $R^2$ are, individually, identical or different, in some cases substituted, alkylene radicals having from 2 to 10 carbon atoms, preferably from 2 to 3 carbon atoms, T is the active hydrogen depleted residue of a trifunctional initiator molecule for the alkylene oxide polymerization, and x, x', y, y', z and z' are identical or different integers between 1 and 60, inclusive, so that the total yields an amine number from 20 to 250.

The cited polyoxyalkylene polyamines can be used individually or as mixtures. Preferably mixtures of polyoxyalkylene polyamines of formulas (I) and (II) and those of formulas (III) and (IV) can be used, whereby the mixing ratios of (I):(II) or (III):(IV) lie in the range from 99.5:0.5 to 20:80, preferably from 99.5:0.5 to 50:50.

The polyoxyalkylene polyamines which can be used in accordance with the invention can be prepared by means of known methods.

Typical methods are the cyanoalkylation of polyoxyalkylene polyols and the subsequent hydrogenation of the nitrile which is formed (U.S. Pat. No. 3,267,050) or the amination of polyoxyalkylene polyols with amines or ammonia in the presence of hydrogen and catalysts (DE No. 12 15 373).

Suitable polyoxyalkylene polyols can themselves be obtained through the addition of one or more cyclic ethers having from 2 to 10 carbon atoms, preferably from 2 to 3 carbon atoms, for example tetrahydrofuran, oxetane, 1,2- or 2,3-butylene oxide, styrene oxide, and preferably ethylene oxide and 1,2-propylene oxide to an initiator, which contains in bonded form from 2 to 5, preferably from 2 to 3 reactive hydrogen atoms.

Typical initiators are: water, ammonia, alkanolamines such as ethanolamine, diethanolamine, N-methyl- and N-ethylethanolamine, N-methyl- and N-ethyldiethanolamine, and triethanolamine, and preferably polyfunctional, more preferably, di- and/or trifunctional alcohols such as ethylene, 1,2- and 1,3-propylene, diethylene, dipropylene, 1,4-butylene, and 1,6-hexamethylene glycols as well as glycerine, trimethylolpropane, and pentaerythritol.

To prepare the isocyanate mixtures claimed in the invention, crude MDI is suitable which has an MDI (diphenylmethane diisocyanate) content of from 30 to 90 weight percent based on the total weight. Crude MDI having an MDI content from 55 to 90 weight percent, preferably from 60 to 85 percent, can be reacted directly with the polyoxyalkylene polyamines (A) using process version B1. Crude MDI having an MDI content from 30 to 85 weight percent, preferably from 40 to 60 weight percent, is generally used to dilute the urea group-containing MDI in process version B2 and, optionally, also to dilute urea group-containing crude MDI having a high MDI content.

Suitable MDI isomers are 4,4'-, 2,4'-, and 2,2'-MDI. Mixtures of at least two of these isomers, in particular 4,4'- and 2,4'-MDI are preferred, since they are liquid at room temperature in contrast with the essentially pure compounds or since they flow better. For example, MDI mixtures comprised of 40 to 98 weight percent, preferably 50 to 96 weight percent, and more preferably 60 to 85 weight percent 4,4'-MDI, 60 to 2 weight percent, preferably 50 to 2 weight percent, and more preferably 40 to 14 weight percent 2,4'-MDI, and 0 to 2 weight percent, preferably 0 to 1 weight percent, 2,2'-MDI have proved successful.

In order to prepare the urea group-containing polyisocyanate mixtures claimed in the invention, the polyoxyalkylene polyamines and crude MDI or MDI isomer mixtures are reacted in such amounts that the $NCO:NH_2$-group ratio is from 1:0.005 to 1:0.35, preferably from 1:0.1 to 1:0.2.

The crude MDI having an MDI content from 55 to 90 weight percent and the polyoxyalkylene polyamine (A) is mixed in process version B1 at temperatures from 10° to 120° C., preferably from 60° to 90° C. with high turbulence, for example by stirring at agitator speeds of from 200 to 1500 rpm and is simultaneously reacted. After a reaction time of 0.25 to 60 minutes, preferably from 5 to 15 minutes, the reaction mixture is allowed to cool.

When the polyisocyanate mixtures claimed in the invention are used to prepare flexible polyurethane foams, process version B2 is preferably used. Here the MDI or preferably the MDI isomer mixture and the polyoxyalkylene polyamines (A) are mixed as described above for B1 at temperatures from 0° to 120° C., preferably from 0° to 90° C., and reacted. After a reaction time of from 0.25 to 60 minutes, preferably from 0.25 to 15 minutes, the urea group-containing reaction mixture is cooled to temperatures from 20° to 80° C. and diluted with crude MDI having an MDI content of from 30 to 85 weight percent until the isocyanate group content of from 15 to 30 weight percent claimed in the invention is reached. When using from 40 to 90 weight parts of a urea group-containing MDI mixture, generally from 60 to 10 weight parts crude MDI having an MDI content between 4 and 65 weight percent are necessary for this.

The liquid, urea group-containing polyisocyanate mixtures claimed in the invention are storage stable at 15° C. for several months. They are used to prepare dense or cellular polyurethane and/or polyisocyanurate plastics.

Since the polyisocyanate mixtures—as already discussed—unexpectedly significantly improve the resistance to aging at high temperatures and high humidities and, in particular, also significantly improve the tensile strength properties of flexible polyurethane foams having low densities, their use is preferred for the preparation of said foams.

In order to prepare flexible polyurethane foams, the liquid, urea group-containing polyisocyanate mixtures claimed in the invention are reacted with polyhydroxyl compounds and, in some cases, chain extenders, in the presence of blowing agents, as well as, optionally, auxiliaries and/or additives. To prepare said foams, the exclusive use of the polyisocyanate mixtures claimed in the invention is preferred. However, in order to obtain certain properties, for example to improve resistance to light, flowability, the percentage of open cells, etc., it may be advantageous to mix the polyisocyanate mixtures claimed in the invention with lesser amounts of conventional, optionally modified polyisocyanates, for example with up to 40 weight parts per 100 weight parts of the polyisocyanate mixtures claimed in the invention. Aliphatic, cycloaliphatic, arylaliphatic, and preferably aromatic polyisocyanates can be used for this purpose. Specific examples are: aliphatic diisocyanates such as ethylene diisocyanate, 1,4-tetramethylene diisocyanate, 1,6-hexamethylene diisocyanate, and 1,12-dodecane diisocyanate; cycloaliphatic diisocyanates such as cyclohexane 1,3-diisocyanate and cyclohexane 1,4-diisocyanate as well as various mixtures of these isomers, 1-isocyanato-3,3,5-trimethyl-5-isocyanatomethylcyclohexane, 2,4- and 2,6-hexahydrotoluene diisocyanate, as well as various mixtures of these isomers, 4,4'- and 2,4'-diisocyanatodicyclohexylmethane; aromatic diisocyanates such as 1,3- and 1,4-phenylene diisocyanate, 2,4- and 2,6-toluene diisocyanate as well as various mixtures of these isomers and naphthalene 1,5-diisocyanate. In addition, modified polyisocyanates may be used, for example, carbodiimide, allophanate, biuret, ester, isocyanurate, and preferably urethane group-containing polyisocyanates of the organic polyisocyanates cited as typical examples. The commercially easily available 2,4- and/or 2,6-toluene diisocyanates as well as urethane group-containing polyisocyanates based on 2,4- and 2,6-toluene diisocyanate, 2,2'-, 2,4'-, and 4,4'-MDI and polymeric MDI are preferred for blending.

Preferably conventional linear and/or branched polyester polyols and more preferably polyether polyols having molecular weights from 200 to 8000, preferably from 800 to 5000, and more preferably from 1800 to 3500 are used as the polyhydroxyl compounds to prepare the flexible polyurethane foams. However, other hydroxyl group-containing polymers having the above molecular weights can also be used, for example, polyester amides, polyacetals, and/or polycarbonates, in particular those prepared from diphenyl carbonate and 1,6-hexanediol by means of transesterification.

The polyester polyols can optionally be prepared from dicarboxylic acids, preferably aliphatic dicarboxylic acids having from 2 to 12, preferably 4 to 8, carbon atoms in the alkylene radical and from polyfunctional alcohols having from 2 to 10, preferably 2 to 6 carbon atoms, preferably diols. Typical examples are aliphatic dicarboxylic acids such as glutaric acid, pimelinic acid, suberic acid, azeleic acid, sebacic acid, undecanedioic acid, dodecanedioic acid, and, preferably, adipic acid as well as mixtures of succinic, glutaric and adipic acid, and aromatic dicarboxylic acids such as phthalic acid and terephthalic acid. Examples of polyfunctional, in particular di- and trifunctional alcohols are: ethylene glycol, diethylene glycol, 1,2;1 - or 1,3-propanediol, dipropylene glycol, neopentyl glycol, 1,10-decanediol, glycerine, trimethylolpropane, and, preferably 1,4-butanediol, 1,6-hexanediol, and mixtures of 1,4-butanediol, 1,5-pentanediol, and 1,6-hexanediol. When polyfunctional, in particular trifunctional, alcohols are used to prepare the polyester polyols, their content is preferably calculated such that the functionality of the resulting polyester polyols is a maximum of 6, preferably of from 2 to 4.

The polyester polyols have molecular weights from 500 to 2800, preferably from 1000 to 2000, and hydroxyl numbers from 40 to 280, preferably from 50 to 120.

However, polyether polyols prepared by means of the cationic polymerization of one or more alkylene oxides having from 2 to 4 carbon atoms in the alkylene radical or by means of an anionic polymerizaion of cyclic ethers or mixtures with alkylene oxide and an initiator having from 2 to 4, preferably 2 to 3 active hydrogen atoms, are preferably used as the polyhydroxyl compounds.

Suitable alkylene oxides and cyclic ethers are, for example, tetrahydrofuran, oxetane, 1,2- or 2,3-butylene oxide, styrene oxide, and preferably ethylene oxide and 1,2-propylene oxide. The alkylene oxides can be used individually or in combination, alternatingly added sequentially or as mixtures.

Typical initiators are, for example: water, organic dicarboxylic acid as succinic acid, adipic acid, phthalic acid, and terephthalic acid, aliphatic and aromatic diamines, optionally N-mono, N,N- and N,N'-dialkyl-substituted with alkyl groups having from 1 to 4 carbon atoms such as, optionally, mono- and dialkyl-substituted ethylenediamine, diethylenetriamine, triethylenetetramine, 1,3-propanediamine, 1,3- or 1,4-butanediamine, 1,2-, 1,3-, 1,4-, 1,5-, and 1,6-hexanediamine, phenylenediaminies, 2,4- and 2,6-toluenediamine, and 4,4'-, 2,4'-, and 2,2'-diaminodiphenylmethane; and monoamines such as methylamine, ethylamine, isopropylamine, butylamine, benzylamine, aniline, the toluidines and naphthylamines. Particularly preferred in the group cited above are: N,N,N',N'-tetrakis(2-hydroxyethyl)ethylenediamine, N,N,N',N'-tetrakis(2-hydroxypropyl)ethylenediamine, N,N,N',N''',N''-pentakis(2-hydroxypropyl)diethylenetriamine, phenyldiisopropanolamine, and higher molecular weight oxyalkylene adducts of aniline.

Further initiators are: alkanolamines such as ethanolamine, diethanolamine, N-methyl- and N-ethyldiethanolamine, N-methyl and N-ethyldipropanolamine, and triethanolamine, hydrazine, and hydrizides. Preferably used are polyfunctional, more preferably di- and trifunctional alcohols such as ethylene glycol, 1,2- and 1,3-propanediol, diethylene glycol, dipropylene glycol, 1,4-butanediol, 1,6-hexamethylene glycol, glycerine, trimethylolpropane, and pentaerythritol.

Typical examples of the polyesteramides are the primarily linear condensates obtained from polyfunctional saturated and unsaturated carboxylic acids, or their anhydrides, and polyfunctional saturated and unsaturated aminoalcohols, or mixtures of polyfunctional alcohols with aminoalcohols and polyamines.

Typical polyacetals are compounds which can be prepared from formaldehyde and glycols, such as diethyene glycol, triethylene glycol, 4,4'-dihyoxydiphenyldimethylmethane and hexanediol. Suitable polyacetals can also be prepared by means of the polymerization of cyclic acetals.

Typical hydroxyl group-containing polycarbonates are those of the essentially known type, for example those which can be prepared by means of the reaction of diols such as 1,3-propanediol, 1,4-butanediol, 1,6-hexanediol, diethylene glycol, triethylene glycol, or tetraethylene glycol with phosgene or diarylcarbonates, for example, diphenylcarbonate.

The polyhydroxyl compounds can be used individually or in the form of mixtures. For example, mixtures of polyester and polyether polyols have proven to be successful, whereby the ratio of the components can vary greatly depending on the intended application of the polyurethane foam which is to be produced, for example the polyester/polyether polyol weight ratio can vary from 20:80 to 80:20.

In some cases it may be preferably to use additional chain extenders in addition to the cited polyhydroxyl compounds in order to prepare the polyurethane foam. Typical chain extenders are polyfunctional, in particular di- and trifunctional, compounds having molecular weights from 17 to 600, preferably from 60 to 300. For example, di- and trialkanolamines such as diethanolamine and triethanolamine, aliphatic and aromatic diamines such as ethylenediamine, 1,4-butylenediamine, 1,6-hexamethylenediamine, 4,4'-diaminodiphenylmethane, 3,3'-dialkyl-substituted 4,4'-diaminodiphenylmethanes, 2,4-, and 2,6-toluenediamine, and, preferably, aliphatic diols and triols having from 2 to 6 carbon atoms such as ethylene glycol, 1,4-butanediol, 1,6-hexamethylene glycol, glycerine, and trimethylolpropane are preferably used.

When chain extenders are used, said extenders are used in amounts from 0.05 to 10 weight parts, preferably from 0.1 to 3 weight parts per 100 weight parts of the polyhydroxyl compounds.

One of the blowing agents which can be used to prepare the flexible polyurethane foams is water, which reacts with isocyanate groups to form carbon dioxide. The preferably used amounts of water are from 0.1 to 8 weight parts, more preferably from 1.5 to 5 weight parts based on 100 weight parts polyhydroxyl compound.

Physical blowing agents can also be used mixed with water. Suitable are liquids which are inert relative to the polyisocyanate mixtures claimed in the invention and which have boiling points under 100° C., preferably under 50° C., more preferably between −50° C. and 30° C. at atmospheric pressure, so that they volatilize due to the heat produced in the exothermic addition polymerization. Examples of such preferably used liquids are hydrocarbons such as pentane, n- and isobutane and propane; ethers such as dimethyl ether and diethyl ether; ketones such as acetone and methylethyl ketone; ethyl acetate; and, preferably, halogenated hydrocarbons such as methylene chloride, trichlorofluoromethane, dichlorodifluoromethane, dichloromonofluoromethane, dichlorotetrafluoroethane, and 1,1,2-trichloro-1,2,2-trifluoroethane. Mixtures of these low boiling point liquids with one another and with other substituted or unsubstituted hydrocarbons can also be used.

The amount of physical blowing agents necessary in addition to the water can be determined in a simple manner as a function of the desired foam density. This amount ranges from 0 to 50 weight parts, preferably from 0 to 20 weight parts, per 100 weight parts polyhydroxyl compound. In some cases it may be desirable to mix the polyisocyanate mixture claimed in the invention with the physical blowing agent, thereby reducing viscosity.

In order to accelerate the reaction between the polyhydroxyl compounds, water, and optional chain extenders and the polymeric MDI-based polyisocyanate mixtures claimed in the invention, conventional polyurethane catalysts are incorporated in the reaction mixture. Preferably used are alkaline polyurethane catalysts, for example, tertiary amines such as dimethylbenzylamine, dicyclohexylmethylamine, dimethylcyclohexylamine, bis(2-dimethylaminoethyl)ether, bis(dimethylaminopropyl)urea, N-methyl- or N-ethylmorpholine, dimethylpiperazine, pyridine, 1,2-dimethylimidazol, 1-azabicyclo(3,3,0)octane, dimethylaminoethanol, 2-(N,N-dimethylaminoethoxy)ethanol, N,N',N''-tris(-dialkylaminoalkyl)hexahydrotriazine, for example N,N',N''-tris(dimethylaminopropyl)-s-hexahydrotriazine, and more preferably triethylenediamine. However, meta salts such as iron-II-chloride, zinc chloride, lead octoate, and, preferably, tin salts such as tin dioctoate, tin diethylhexoate, and dibutyltin dilaurate are also suitable, as well as, in particular, mixtures of tertiary amines and organic salts of tin. It is desirable to use from 0.1 to 10 weight percent, preferably from 0.3 to 3 weight percent catalyst based on the tertiary amines and/or 0.01 to 0.5 weight percent, preferably from 0.03 to 0.25 weight percent metal salts, based on the weight of the polyhydroxyl compounds.

Auxiliaries and/or additives can also be incorporated into the reaction mixture. Typical are stabilizers, agents to protect against hydrolysis, or regulators, fungistats and bacteriostats, colorants, pigments, fillers, surfactants, and flame retardants.

For example, surfactants which aid in homogenizing the starting materials and which may also be suitable for regulating the cell structure of the foams can be used. Typical are: siloxane/oxyalkylene copolymers and other organopolysiloxanes, oxyethylated alkylphenols, oxyethylated fatty alcohols, paraffin oils, castor oil, ricinoleic acid ester, and Turkey Red oil. Typically these are used in amounts ranging from 0.05 to 5, preferably, from 0.1 to 2 weight parts per 100 weight parts polyhydroxyl compound.

Typical flame retardants are phosphorus- and/or halogen-containing compounds such as tricresyl phosphate, tris-2-chloroethyl phosphate, tris-chloropropyl phosphate and tris-2,3-dibromopropyl phosphate.

In addition to the halogen-substituted phosphates cited above, inorganic flame retardants can also be used, for example, antimony trioxide, arsenic oxide, ammonium phosphate, and calcium sulphate, or melamine. Such flame retardants are utilized to make the flexible polyurethane foams flame resistant.

Generally it has been found to be advantageous to use from 5 to 50 weight parts, preferably from 5 to 20 weight parts, of the cited flame retardants per 100 weight parts polyhydroxyl compound.

In order to prepare the flexible polyurethane foams, the polyisocyanate mixtures claimed in the invention, polyhydroxyl compounds, and optional chain extenders are reacted in the presence of catalysts, blowing agents, and, optionally auxiliaries and/or additives at initial temperatures from 0° to 70° C., preferably from 15° to 50° C., in such amounts that for each NCO group, from 0.5 to 2, preferably from 0.8 to 1.3 reactive hydrogen atoms and more preferably approximately one reactive hydrogen atom is present bonded onto the polyhydroxyl compound and optional chain extenders are present such that the equivalent ratio of water used as blowing agent to NCO group ranges from 0.5:1 to 5:1, preferably from 0.7:1 to 0.95:1, and more preferably from 0.75:1 to 0.85:1.

The flexible polyurethane foams are prepared using a one-shot process, whereby the starting components, auxiliaries, and additives can be fed into a mixing chamber using one or more feed nozzles and such that they are mixed intensively in the mixing chamber. However, it has been found to be particularly desirable and preferred to use a two-component feed process. In this process the polyhydroxyl compound, catalysts, blowing agent, and optional chain extenders, auxiliaries, and/or additives are combined in the so-called A component, and the B component contains the polyisocyanate mixture claimed in the invention, optionally mixed with physical blowing agents, auxiliaries and/or additives. One advantage of this is that the A and B components can be transported in a space-saving manner and can be stored for a limited time, so that all is needed is to mix them intensively prior to preparing the flexible polyurethane foams. The reaction mixtures can be expanded in open or closed molds.

The flexible polyurethane foams prepared from the liquid, urea group-containing polyisocyanate mixtures have densities from 10 to 150 kg/m$^3$, preferably from 20 to 70 kg/m$^3$ and are characterized by high resistance to deterioration of mechanical properties at elevated temperatures and humidities.

The parts cited in the examples are parts by weight.

EXAMPLE 1

Preparation of the urea group-containing polyisocyanate mixture

Forty-two and three-tenths parts of a block copolyoxyalkylene polyamine having an amine number of 27 and a hydroxyl number of 0 prepared through the animation of a polyetherdiol based on dipropylene glycol/1,2-propylene oxide/ethylene oxide was added within 30 minutes to 100 parts of 75:25 weight ratio mixtures of 4,4'- and 2,4'-MDI, respectively, at 80° C. with vigorous mixing (1200 rpm).

After a reaction time of 15 minutes, the reaction mixture was allowed to cool to 40° C. and was diluted in a 80:20 weight ratio with crude MDI having an MDI content of 47 weight percent. The result was a dark brown, llquid, homogenous polyisocyanate mixture having an NCO-group content of 24.5 weight percent.

COMPARISON EXAMPLE A

Preparation of a urethane group-containing polyisocyanate mixture

The procedure from Example 1 was used, however instead of using the block copolyoxyalkylene polyamine, the precursor polyoxyethylene polyoxypropylene glycol was used.

The results was a dark brown, homogeneous liquid having an NCO-group content of 24.6 weight percent.

EXAMPLE 2

Foam Preparation

Flexible polyurethane foam was prepared from two components.

A Component:

Mixture of 90.35 parts of a glycerine-initiated polyoxypropylene-polyoxyethylene triol having 20 weight percent terminal polyoxyethylene groups and a hydroxyl number of 26, 2.8 parts water, 0.35 parts of a 33 weight percent solution of triethylene diamine in dipropylene glycol, 0.2 parts bis(2-dimethylaminoethyl)ether, 0.2 parts 2-dimethylaminoethanol and 6 parts trichlorofluoromethane.

B Component:

58.5 weight parts of the polyisocyanate mixture of Example 1.

The A and B components were mixed intensively for 8 seconds at 23° C. Eight hundred and eighty grams of the reactable mixture was filled into a metal mold heated to 50° C. and having internal dimensions of 40×40×10 cm and was allowed to expand in the closed mold.

An elastic molded part having a density of 51 g/l was obtained.

COMPARISON EXAMPLE B

Comparative Foam Preparation

For comparative purposes, a flexible polyurethane foam was prepared as follows.

A Component: as in Example 2

B Component: 58.3 weight parts of the polyisocyanate mixture of Comparison Example A.

The molded part was prepared as in Example 2.

The molded part per Example 2 and per Comparison Example B had comparable values for elongation, tensile strength, compression set, and hardness.

In order to determine mechanical properties after aging at elevated temperature and humidity, the molded parts were subjected to the following test procedures:

Aging in an Autoclave

Five hours at 120° C. with saturated steam and subsequently, 24 hours at 70° C. in a dry oven with fresh air circulation.

Elevated Temperature Aging

Twenty-two hours at 140° C. in a dry oven.

The following Table 1 shows the percent reduction in compression set per Din 53 572 in compression hardness per Din 53 577, and in tensile strength per DIN 53 571. This data shows that the loss in all properties tested was less for the urea-containing polyisocyanate derived products compared to comparable urethane-containing products of the prior art.

TABLE I

| | Loss of Physical Properties on Aging | |
|---|---|---|
| Product of: | Example 2 | Comparison Example B |
| Autoclaving: | | |
| Compression set | 2% | 29% |
| Compression Hardness | 36% | 45% |
| Heat Aging: | | |
| Tensile Strength | 7% | 19% |

The embodiments of the invention in which an exclusive privilege or property is claimed are defined as follows:

1. Urea group-containing polyisocyanate mixtures which are liquid at room temperature and have an isocyanate group content of from 15 to 30 weight percent and a diphenylmethane diisocyanate content of from 55 to 90 weight percent, obtained by reacting at a temperature of 80° C. or less in such amounts that the NCO:NH$_2$ equivalent ratio is from 1:0.005 to 1:0.35, a polyoxyalkylene polyamine having an amine functionality of from 2 to 5 and an amine number from 20 to 250 with an excess of a diphenylmethane diisocyanate isomer mixture containing from 40 to 98 weight percent 4,4'-diphenylmethane diisocyanate, from 60 to 2 weight percent 2,4'-diphenylmethane diisocyanate, and from 0 to 2 weight percent 2,2'-diphenylmethane diisocyanate, said weight percents being based on the total weight of the diphenylmethane diisocyanate mixture.

2. Urea group-containing polyisocyanate mixtures of claim 1 wherein the polyoxyalkylene polyamine has structures selected from the group containing one of the following formulas:

$$H_2N-(R^2O)_x-R^1-NH_2,$$

(I)

$$H_2N-R^1-(OR^2)_x-NH-(R^2O)_y-R^1-NH_2,$$

(II)

$$H_2N-R^1-(OR^2)_x-T\begin{matrix}(R^2O)_y-R^1-NH_2\\ \\(R^2O)_z-R^1-NH_2\end{matrix},$$

(III)

and
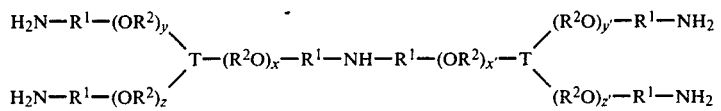
(IV)
wherein
R[1] and R[2] are individually identical or different, alkylene radicals having from 2 to 10 carbon atoms,
T is an active hydrogen containing compound depleted of the active hydrogen, and
x, x', y, y', z and z' are identical or different integers between 1 and 60, inclusive.
* * * * *

UNITED STATES PATENT AND TRADEMARK OFFICE
CERTIFICATE OF CORRECTION

PATENT NO. : 4,611,083
DATED : September 9, 1986
INVENTOR(S) : INGOLF BUETHE ET AL It is certified that error appears in the above-identified patent and that said Letters Patent is hereby corrected as shown below:

On first page of patent for bibliographic data
under ICI/REPAT Code 30 Foreign Application
Priority Data: correct 3342564 to "3342864."

Signed and Sealed this

Eleventh Day of November, 1986

Attest:

DONALD J. QUIGG

Attesting Officer    Commissioner of Patents and Trademarks